(12) United States Patent
Liang et al.

(10) Patent No.: US 10,045,705 B2
(45) Date of Patent: Aug. 14, 2018

(54) HAND-HELD, MEDICAL, MULTI-CHANNEL BIOLOGICAL INFORMATION COLLECTION MOBILE TERMINAL SYSTEM

(75) Inventors: Zhiwei Liang, Guangdong (CN); Zhangjin Su, Guangdong (CN); Lili He, Guangdong (CN); Xiaoping Lai, Guangdong (CN)

(73) Assignee: DONGGUAN MATHEMATICAL ENGINEERING ACADEMY OF CHINESE MEDICINE AND GUANGZHOU UNIVERSITY OF TRADITIONAL CHINESE MEDICINE AND GUANGZHOU UNIVERSITY OF TRADITIONAL CHINESE MEDICINE, Dongguan, Guangdong (CN)

( * ) Notice: Subject to any disclaimer, the term of this patent is extended or adjusted under 35 U.S.C. 154(b) by 515 days.

(21) Appl. No.: 14/345,262

(22) PCT Filed: Sep. 10, 2012

(86) PCT No.: PCT/CN2012/081192
§ 371 (c)(1),
(2), (4) Date: Mar. 17, 2014

(87) PCT Pub. No.: WO2013/040995
PCT Pub. Date: Mar. 28, 2013

(65) Prior Publication Data
US 2014/0350377 A1 Nov. 27, 2014

(30) Foreign Application Priority Data
Sep. 23, 2011 (CN) .......................... 2011 1 0283962

(51) Int. Cl.
*A61B 5/0404* (2006.01)
*A61B 5/053* (2006.01)
(Continued)

(52) U.S. Cl.
CPC .......... *A61B 5/0404* (2013.01); *A61B 5/0531* (2013.01); *A61B 5/6806* (2013.01);
(Continued)

(58) Field of Classification Search
CPC .................................................... A61B 5/6806
See application file for complete search history.

(56) References Cited

U.S. PATENT DOCUMENTS 6,501,002 B1 * 12/2002 Roe .......................... A47K 7/00
422/402
2002/0045805 A1 * 4/2002 Gopinathan ......... A61B 5/0002
600/300

* cited by examiner

*Primary Examiner* — Luther G Behringer
(74) *Attorney, Agent, or Firm* — Ming Chow; Sinorica, LLC

(57) ABSTRACT

Disclosed is a hand-held, medical, multi-channel biological information acquisition mobile terminal system, comprising two signal sensing gloves RL with a cable end embedded therein, for use in acquiring a variety of biological signals comprising multi-channel interconnected ECG, heart sounds, finger blood volume pulse, and skin impedance etc., the signal sensing gloves RL also comprising a signal acquisition device S, a signal transmission device C connected to the signal acquisition device S, and a mobile terminal T connected wirelessly or with a wired connection. The system has the characteristics of low power consumption, small size, low cost and fewer control channels needed for multi-channel connection; and the system can achieve on-site acquisition of a variety of biological information and the mobile function of electronic health records.

11 Claims, 10 Drawing Sheets

(51) Int. Cl.
*A61B 5/00* (2006.01)
*A61B 5/024* (2006.01)
*A61B 5/0295* (2006.01)
*A61B 5/1455* (2006.01)

(52) U.S. Cl.
CPC ......... *A61B 5/0295* (2013.01); *A61B 5/02427* (2013.01); *A61B 5/14552* (2013.01)

HAND-HELD, MEDICAL, MULTI-CHANNEL BIOLOGICAL INFORMATION COLLECTION MOBILE TERMINAL SYSTEM

TECHNICAL FIELD OF THE INVENTION

The invention relates to the technical field of multi-channel biological information acquisition, in particular to a hand-held, medical, multi-channel biological information acquisition mobile terminal system.

BACKGROUND OF THE INVENTION

With the continuous development of information technology and management philosophy, the hospital information construction has become an important means to enhance the level of hospital management. Popularization of mobile computer and application of wireless network help more and more hospitals to achieve 'patient-centered' management philosophy, so that clinical mobile healthcare has become a hot spot in medical industry information construction at home and abroad.

Biological signals reflect the states of life activities of organisms. The common biological signals comprise ECG, heart sound, blood pressure, blood volume pulse and temperature, etc., while the common biological signal acquisition instruments in large size may not be carried with or used by wearing. Since these biological signals on body surface are acquired by an electrode or by acoustic-electric transduction, or piezoelectric transduction or photoelectric transduction, or connected to a biological signal amplification device and then directly displayed on the screen of a monitor, the activities of the patients are largely limited, resulting in that daily lives and actions of the patients need to be taken care of by all required personnel during biological signal acquisition process. Moreover, the majority of patients may take care of themselves and do some light activities, but long time clinical monitoring makes a certain influence on the activities of the patients, resulting in many applicable crowds unwilling to be monitored.

In addition, in many hospitals, a doctor workstation computer is placed in the doctor's office, so the doctor needs to print the information of the patients out via the computer before going the rounds of the wards, carries with large amounts of paper documents and inspection reports of patients, and reads the information by finding out one by one, resulting in low efficiency. When the doctor needs to make medical orders, the orders are often recorded in the book first and then recorded in an information system after the doctor returns back to the office. As a result, there might be a possibility of transcription error. In order to improve the level of modern management, many hospitals have established or are establishing information system, however the existing hospital information system (HIS) cannot move freely to track full life cycle of medical orders, which especially cannot directly input vital signs information of the patients into the system by a nurse beside a hospital bed, so that the information of nursing records is incomplete and information management for the work of nurses is unable to be achieved.

As can be seen from the above prior art, the existing biological signals acquisition and processing instruments have many inconvenient factors that the instruments have complex structure, larger size, inconvenience to carry with and high cost, and the medical staff may not consult and record electronic health records of the patients at any time while going the rounds of the wards, thus limiting popularization and development of the clinical medical mobilization.

SUMMARY OF THE INVENTION

To overcome shortcomings of the background technology, the invention, provides a hand-held, medical, multi-channel biological information acquisition mobile terminal system, which has the characteristics of low power consumption, small size and low cost, and can achieve on-site acquisition function of a variety of biological information and the mobilization of electronic health records.

The object of the present invention is achieved by the following technical measures: a signal sensing glove for acquiring biological signals is provided, comprising two signal sensing gloves RL for acquiring biological signals comprising ECG which are respectively glove R and glove L, the glove R and the glove L being provided with a signal bus port U, the glove R being connected to the glove L through the signal bus port U.

The object of the present invention is further achieved by: a metal body RP and a metal body YP for acquiring biological signals comprising ECG are respectively embedded on inner walls of the glove R and the glove L, in which the metal body RP is disposed inside the glove R and the metal body YP is disposed inside the glove L; a bus wiring port Rc and a bus wiring port Lc with at least one port wired are respectively embedded on outer walls of the metal body RP and the metal body YP, in this way, the wiring port Rc being disposed outside the glove R and the wiring port Lc being disposed outside the glove L, the wiring port Rc being connected to the metal body RP and the wiring port Lc being connected to the metal body YP; a metal body BP for acquiring biological signals comprising ECG is embedded on an outer wall of at least one of the glove R and the glove L, or a metal body BP and a metal body GP for acquiring biological signals comprising ECG are respectively embedded on the outer walls of the glove R and the glove L, in which the metal body BP is disposed outside the glove R and the metal body GP is disposed outside the glove L; when the wiring port Rc is connected to the wiring port Lc, an electronic element or a signal circuit in the glove R in connection with the wiring port Rc can be communicated with an electronic element or a signal circuit in the glove L in connection with the wiring port Lc by means of a bridged interconnection between the wiring port Rc and the wiring port Lc.

The object of the present invention is further achieved by: the wiring port Rc is in bridged interconnection with the wiring port Lc; and the signal bus port U is connected to the wiring port Rc and the wiring port Lc, communicated with the signal circuit, and also connected to the electrode metal body RP or the metal body YP or the metal body BP and the metal body GP.

The object of the present invention is further achieved by: the metal body RP and the metal body YP are stuck on the skin of upper limbs and communicated with the wiring port Rc and the wiring port Lc by wearing the signal sensing gloves RL distinct in the left and right hands, and then the signal sensing gloves RL are placed on the skin of lower limbs or abdomen adjacent to the lower limbs to make the metal body BP and the metal body GP stick on the skin of lower limbs or abdomen adjacent to the lower limbs, in order to achieve that on one hand the signal bus port U is connected to the metal body RP, the metal body YP and the metal body BP or connected to the metal body RP, the metal body YP, the metal body BP and the metal body GP, but on the one hand is reserved with a connection circuit.

Further, the signal sensing gloves RL are attached with a signal acquisition device S which is attached to one of the glove R and the glove L fixedly or detachably and also connected to the signal bus port U. The glove with the signal acquisition device S attached thereon is provided with a signal transmission device C, the signal transmission device C being provided with a first input port E, a first output port F, a second input port G and a second output port H. The first input port E is connected to a signal output end of the signal acquisition device S. Both the first output port F and the second input port G of the signal transmission device C are served as a reservation circuit, and the second output port H of the signal transmission device C is connected to a signal input end of the signal acquisition device S. Each of the reservation circuits is a device with CPU operational capability, comprising a hand-held mobile terminal T.

Further, the signal sensing gloves R which are glove R and glove L, respectively, together with the signal acquisition device S and the signal transmission device C attached on the gloves and the hand-held mobile terminal T, form a hand-held, medical, multi-channel biological information acquisition mobile terminal system. When the signal acquisition device S is used for acquiring an ECG limb lead electrode, in contact with the human body, of the signal acquisition device S are the metal body RP as the red electrode, the metal body YP as the yellow electrode, the metal body BP as the black electrode and the metal body GP as the green electrode, respectively. On an outer wall of the glove with the signal acquisition device S attached thereon, provided is an electronic pickup stethoscope M fixedly or detachably. There are 1-10 good conductive metal electrodes SKP embedded in a position where an inner wall of the glove R or the glove L is in contact with the fingertip pulp (Shi-xuan acupoint). The glove R and the glove L are respectively provided with electrodes SKP1-SKP5 and electrodes SKP6-SKP10. Light dependent resistors R and light sources or light sources Lmp (Optical network link management protocol) of other wavelengths are embedded in a position where an inner wall of the glove R or the glove L is in contact with the distal finger pulp. The signal acquisition device S is connected to the electronic pickup stethoscope M, multiple electrodes SKP, multiple light dependent resistors R and light sources Lmp (Optical network link management protocol) of visible light wavelength or other wavelengths, respectively.

Further, the signal acquisition device S comprises an ECG acquisition circuit, a heart sound acquisition circuit, a blood volume pulse acquisition circuit, and a skin impedance acquisition circuit. The ECG acquisition circuit comprises a lead input interface, a buffer circuit, a shield actuation circuit, a right leg drive circuit, a pre-amplifier circuit, a two-stage amplifier circuit, a 106 Hz low-pass filter circuit, a 50 Hz trap circuit, and a post-amplifier circuit. The lead input interface is connected to the buffer circuit, and the shield actuation circuit and the right leg drive circuit. The buffer circuit is connected to the pre-amplifier circuit connected to the two-stage amplifier circuit, and the shield actuation circuit and the right leg drive circuit. The two-stage amplifier circuit is connected to the 106 Hz low-pass filter circuit connected to the 50 Hz trap circuit, and the 50 Hz trap circuit is connected to the post-amplifier circuit. The heart sound acquisition circuit comprises a main amplifier circuit, a low-pass filter circuit, a trap circuit, a post-amplifier circuit and an anti-interference device. The main amplifier circuit is connected to the low-pass filter circuit, and the low-pass filter circuit is connected to the trap circuit connected to the post-amplifier circuit. The anti-interference device is connected to two ends of the main amplifier circuit, and the value of the low-pass filter circuit is in the range of 1-6 Hz. The blood volume pulse acquisition circuit comprises a voltage regulator circuit, a red light irradiation circuit, a phototransistor circuit, a bridge circuit, an amplifier circuit and a filter circuit. The red light irradiation circuit is connected to the voltage regulator circuit connected to the phototransistor circuit. The phototransistor circuit is connected to the bridge circuit connected to the amplifier circuit, and the amplifier circuit is connected to the filter circuit. Light dependent resistors R and light sources or light sources LMP of other wavelengths are embedded in a position where an inner wall of the glove R or the glove L is in contact with the distal finger pulp. When the fingers are inserted into the glove, the red light is irradiated on the light dependent resistors R by penetrating the fingers, so that the finger blood volume determines light transmittance of light source penetrating the fingers and also determines resistance variation of the light dependent resistors R so as to achieve the acquisition of the blood volume pulse. The skin impedance acquisition circuit comprises a voltage regulator circuit, a bleeder circuit, a reference resistor, a comparator circuit, a low-pass filter circuit and an output. The voltage regulator circuit is connected to a bleeder circuit connected to the reference resistor. The reference resistor is connected to the comparator circuit connected to the low pass filter circuit. 1-10 good conductive metal electrodes SKP are embedded in a position where an inner wall of the glove R or the glove L is in contact with the fingertip pulp, so, the acquisition of the skin impedance is achieved by pressing the metal electrodes SKP on any two points on the skin, just like by pressing two probes of a universal meter.

Further, the hand-held mobile terminal T comprises a CPU, a data processing unit, a liquid crystal display unit, wireless WIFI or a 3G module.

A method for controlling time division multiplexing circuit gating by a single-channel position control source comprises a pulse counting unit and a multiplex separation unit. The pulse counting unit is provided with an input signal input end CI and at least one control signal output end group COG; each end of at least one control signal output end group COG is set with a binary digit to form a control signal comprising multiple binary digits by a digit combination group; the multiplex separation unit is provided with at least one controlled signal input end group CIG, and each end of at least one controlled signal input end group CIG is set with a binary digit to form a controlled signal address by combination in terms of digit; the multiplex separation unit is also provided with at least one input signal input end group X and an output signal output end Y, and the control signal output end group COG is connected to the controlled signal input end group CIG.

By inputting an amplitude-adjustable timing pulse signal to an input signal input end CI of the pulse counting unit, a varied binary digit is output by at least one control signal output end group COG of the pulse counting unit. The binary digit controls the controlled signal address value of the controlled signal input end group CIG of the multiplex separation unit to vary, regulates gating of at least one input signal input end group X and the output signal output end Y of the multiplex separation unit, and then restores a discrete signal proximity to the original shape of a multi-channel input signal from a signal output by one output signal output end Y by a time division multiplexing calculation method, to achieve the purpose of controlling the time division multiplexing channel function of the multiplex separation unit only by one path of timing pulse signals.

The invention provides a hand-held, medical, multi-channel biological information acquisition mobile terminal system, which has the characteristics of low power consumption, small size and low cost, and can achieve on-site acquisition function of a variety of biological information and the mobilization of electronic health records, wherein the system comprises two signal sensing gloves RL with a cable end embedded therein. One of the gloves is provided with a signal bus port U for pooled connection of acquisition signals. The signal sensing gloves RL further comprise a signal acquisition device S connected to the signal bus port U for use in acquiring a variety of biological signals comprising multi-channel interconnected ECG, heart sounds, finger blood volume pulse, and skin impedance etc., and the signal sensing gloves RL also can save, carry out calculation analysis processing and intuitively display indexes of testee comprising ECG, phonocardiogram, pulse value, heart rate value, degree of blood oxygen saturation, and skin impedance value etc. by connecting with a mobile terminal T wirelessly or with a wired connection through a signal transmission device C.

The invention particularly refers to method for controlling time division multiplexing circuit gating by a single-channel position control source, comprising a pulse counting unit and a multiplex separation unit. An output end of the pulse counting unit is served as a control signal of the multiplex separation unit and connected to a controlled signal input end of the multiplex separation unit, showing as multi-input-single-output or multi-output-single-input.

Compared with the prior art, the invention has the characteristics of stable connection, anti-misoperation and simple operation and fewer control channels needed for multi-channel connection, facilitates the realization of real-time detection and wireless mobile inspection functions of a variety of individual health information for medical staff, even for family and individual in the practice of medical service in community health, helps to optimize the medical procedure, strengthens the medical safety and quality and improves work efficiency.

DETAILED DESCRIPTION OF THE PREFERRED EMBODIMENTS

In order to further understand the characteristics, technical solutions and the achieved specific purposes and functions, the invention will be further described in details as below by embodiments with reference to drawings.

Figure 1:
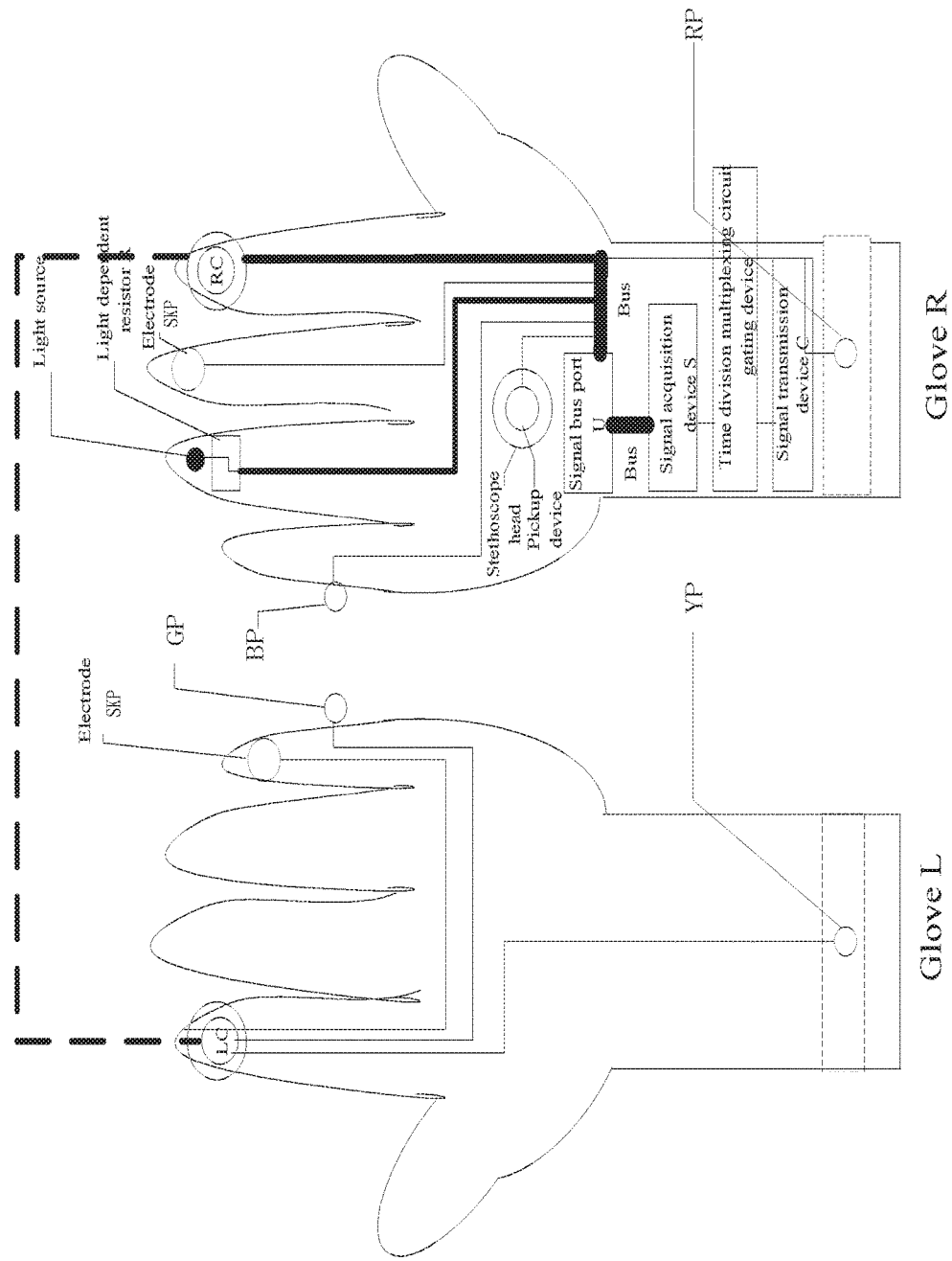
FIG. 1 is a structure diagram of two signal transmission gloves RL according to an embodiment of the invention.
Figure 2:
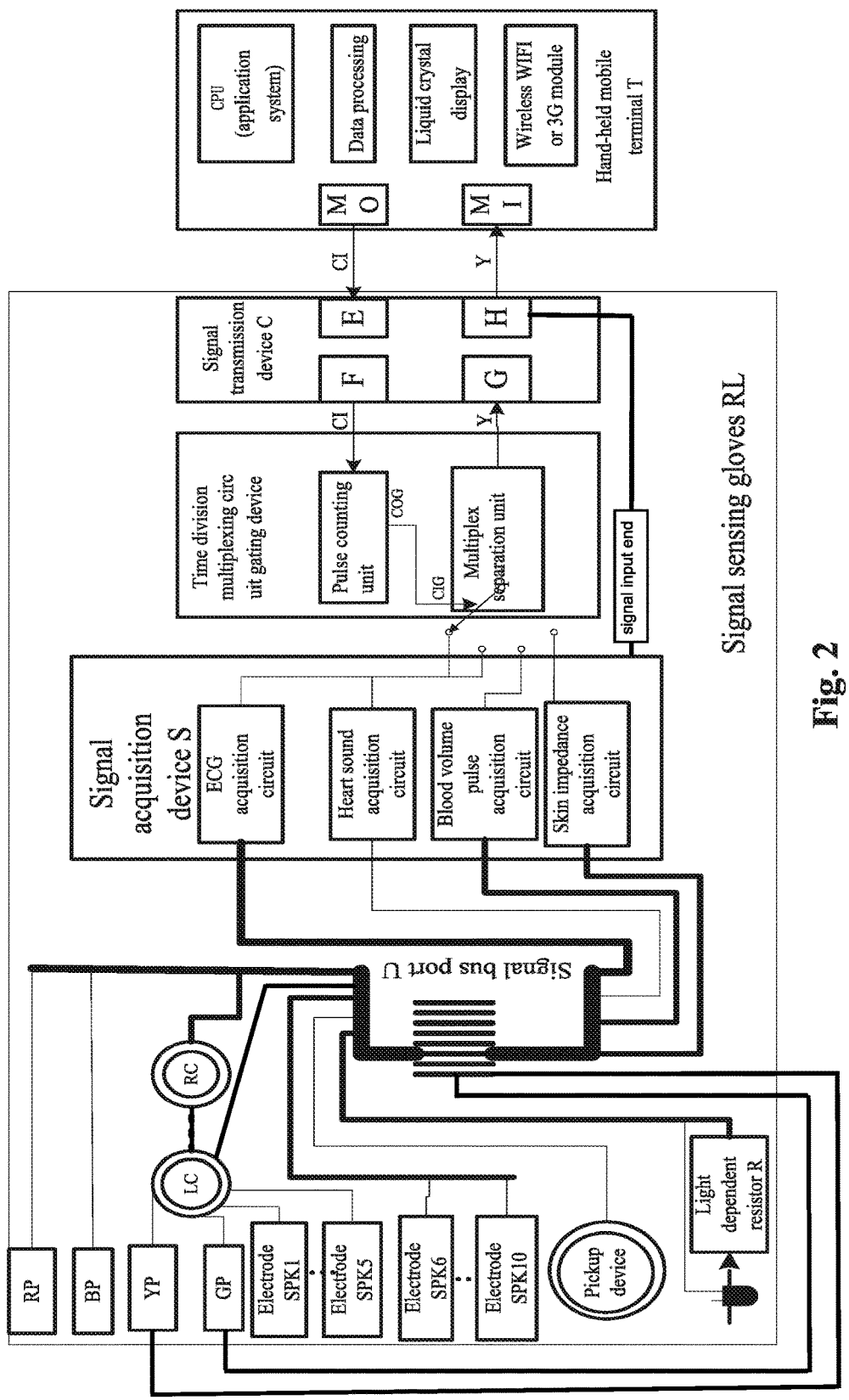
FIG. 2 is a block diagram of an embodiment of a hand-held, medical, multi-channel biological information acquisition mobile terminal system as a whole according to the invention.
Figure 3:
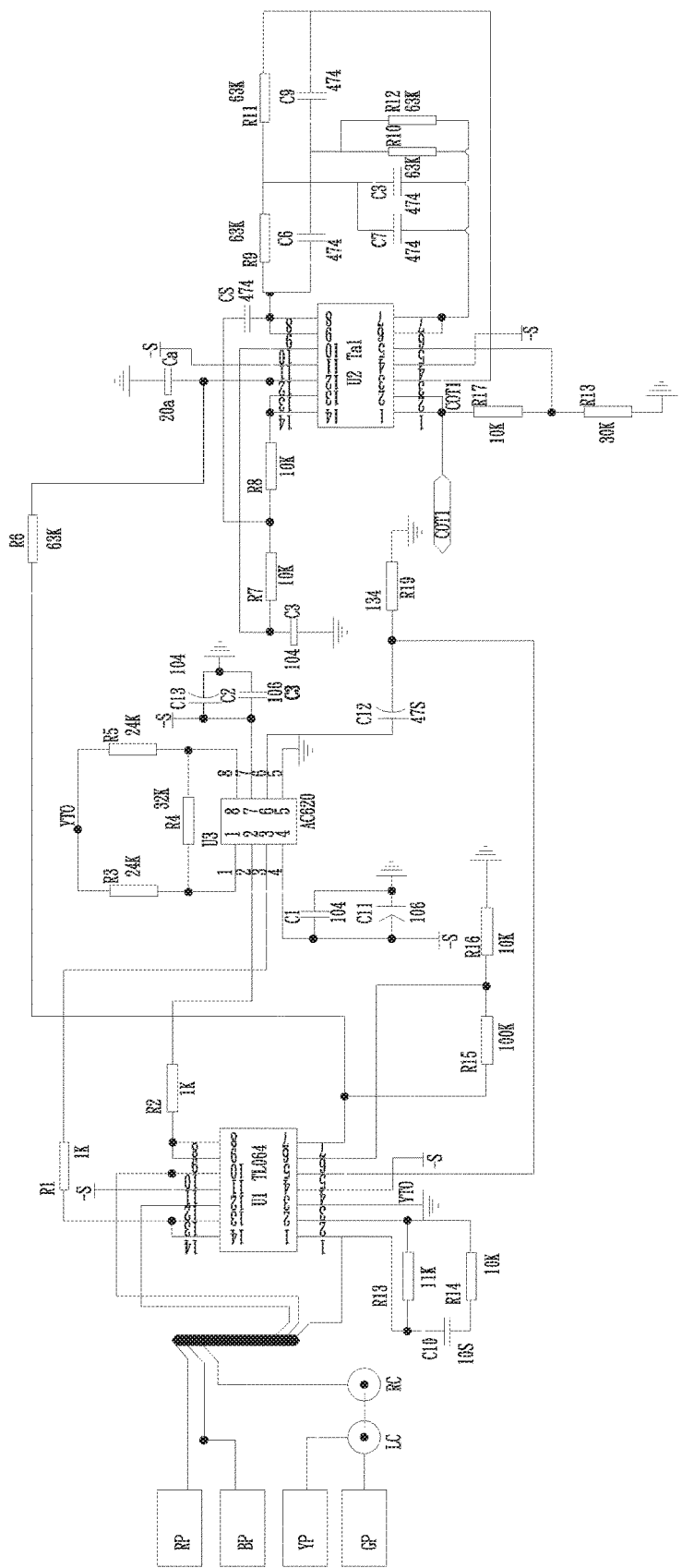
FIG. 3 is a diagram of an ECG acquisition circuit according to an embodiment of the invention.
Figure 4:
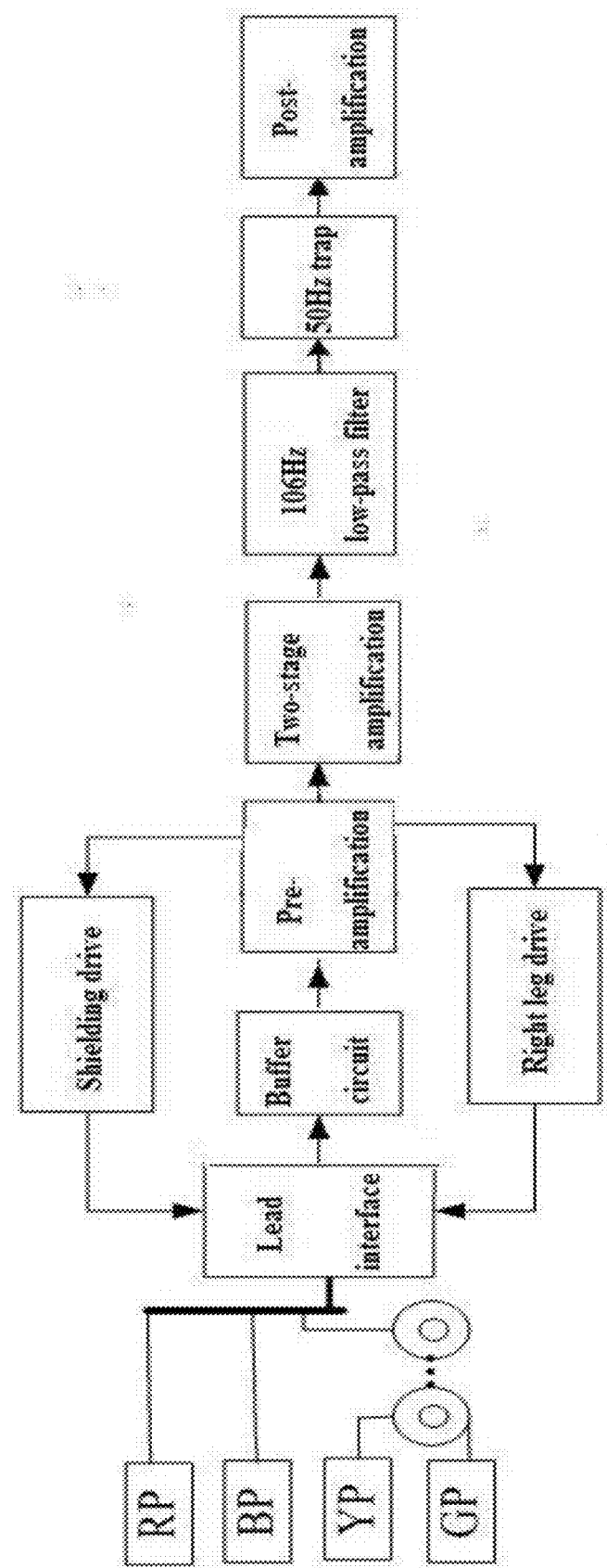
FIG. 4 is a block diagram of the ECG acquisition circuit according to an embodiment of the invention.
Figure 5:
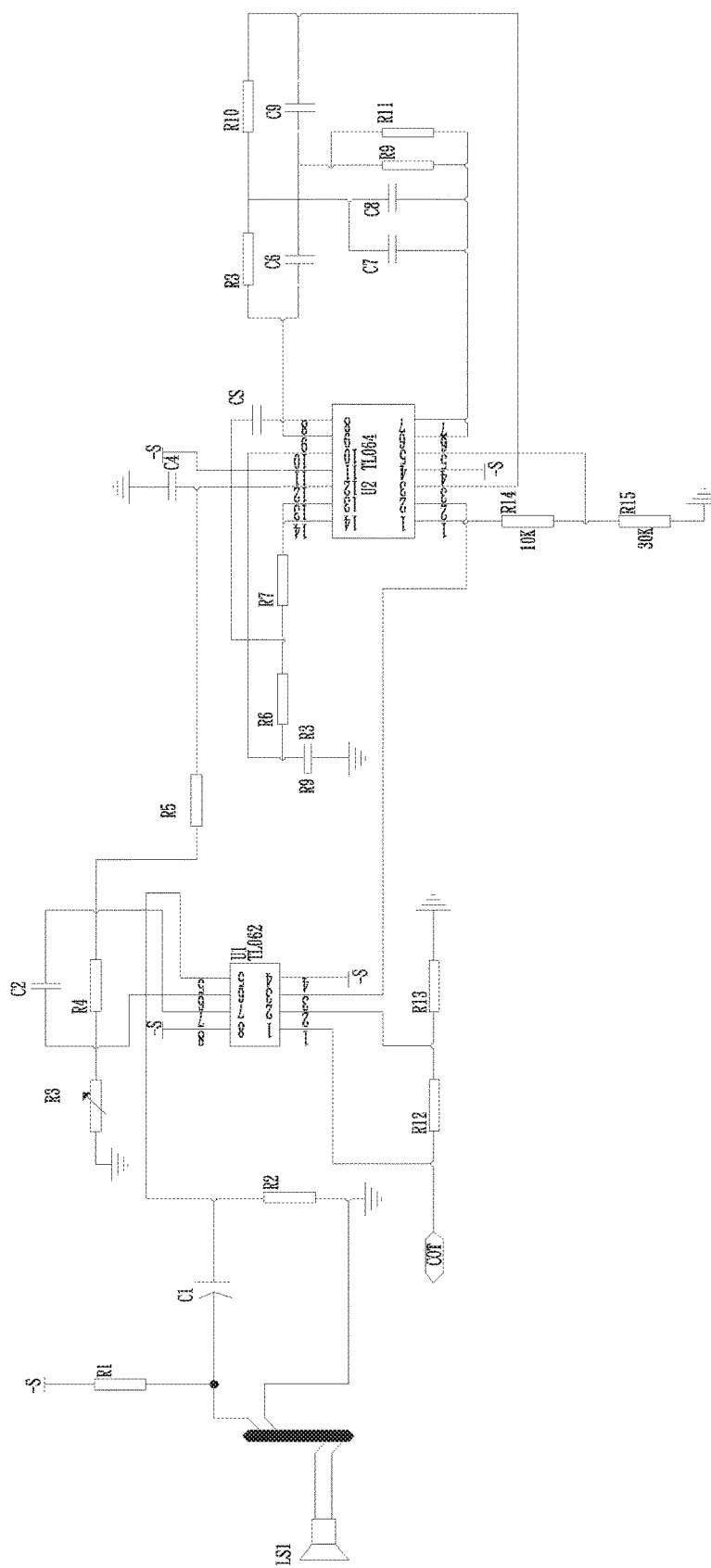
FIG. 5 is a diagram of a heart sound acquisition circuit according to an embodiment of the invention.
Figure 6:
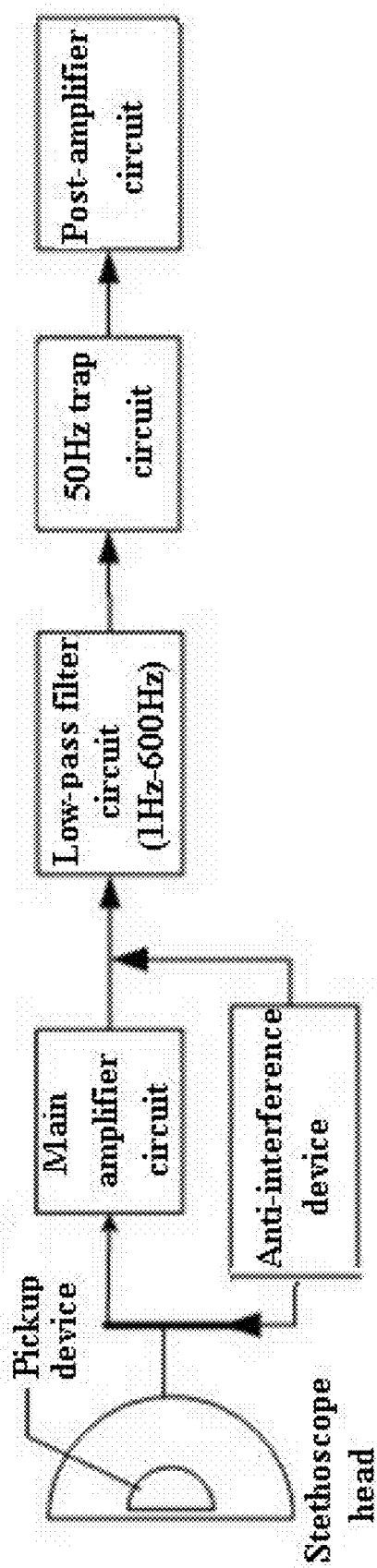
FIG. 6 is a block diagram of heart sound acquisition according to an embodiment of the invention.
Figure 7:
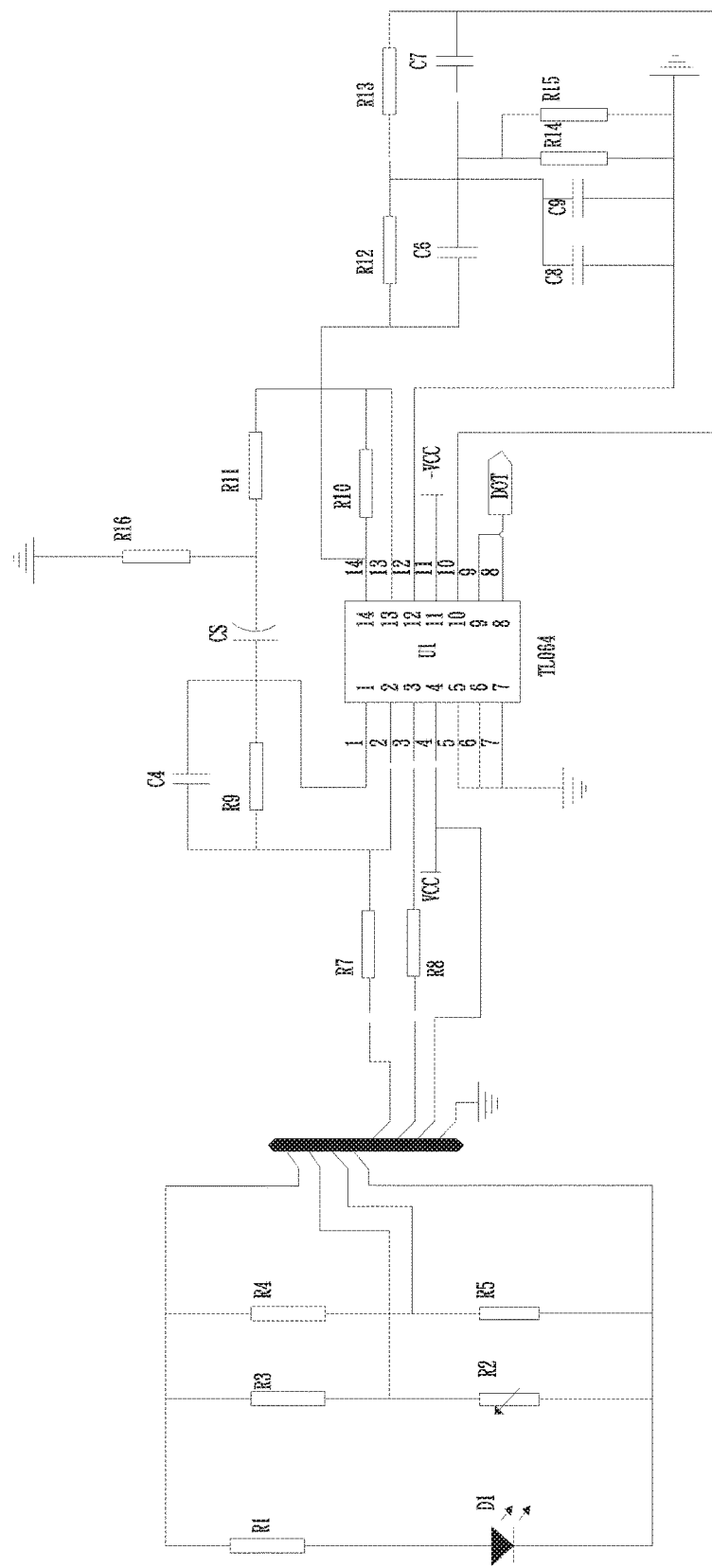
FIG. 7 is a diagram of a blood volume pulse acquisition circuit according to an embodiment of the invention.
Figure 8:
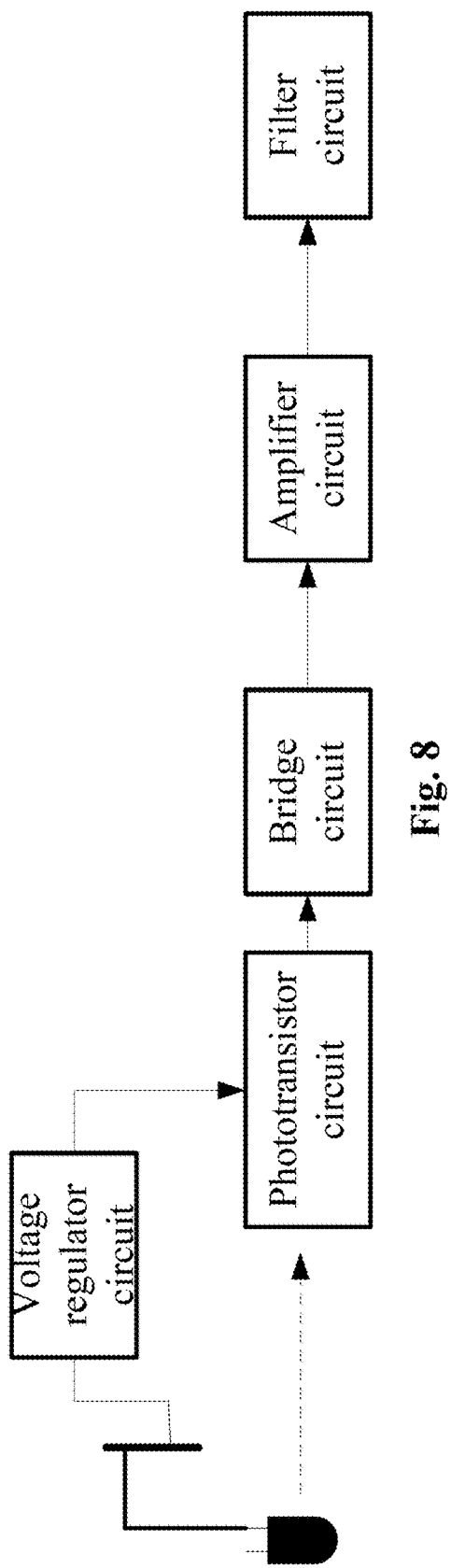
FIG. 8 is a block diagram of the blood volume pulse acquisition circuit according to an embodiment of the invention.
Figure 9:
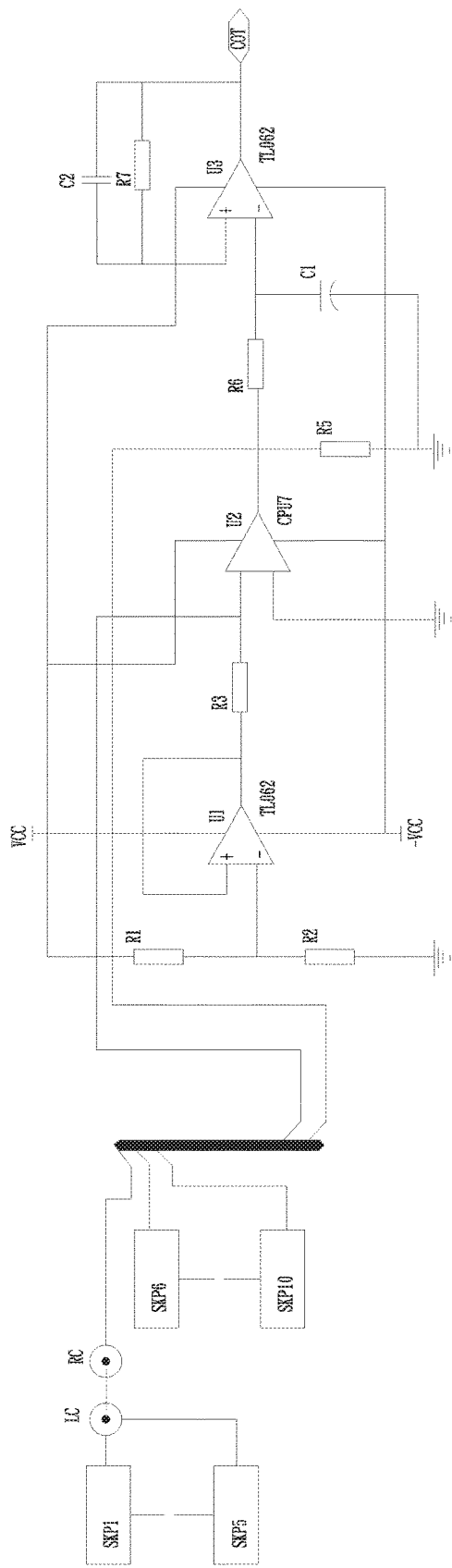
FIG. 9 is a diagram of a skin impedance acquisition circuit according to an embodiment of the invention.
Figure 10:
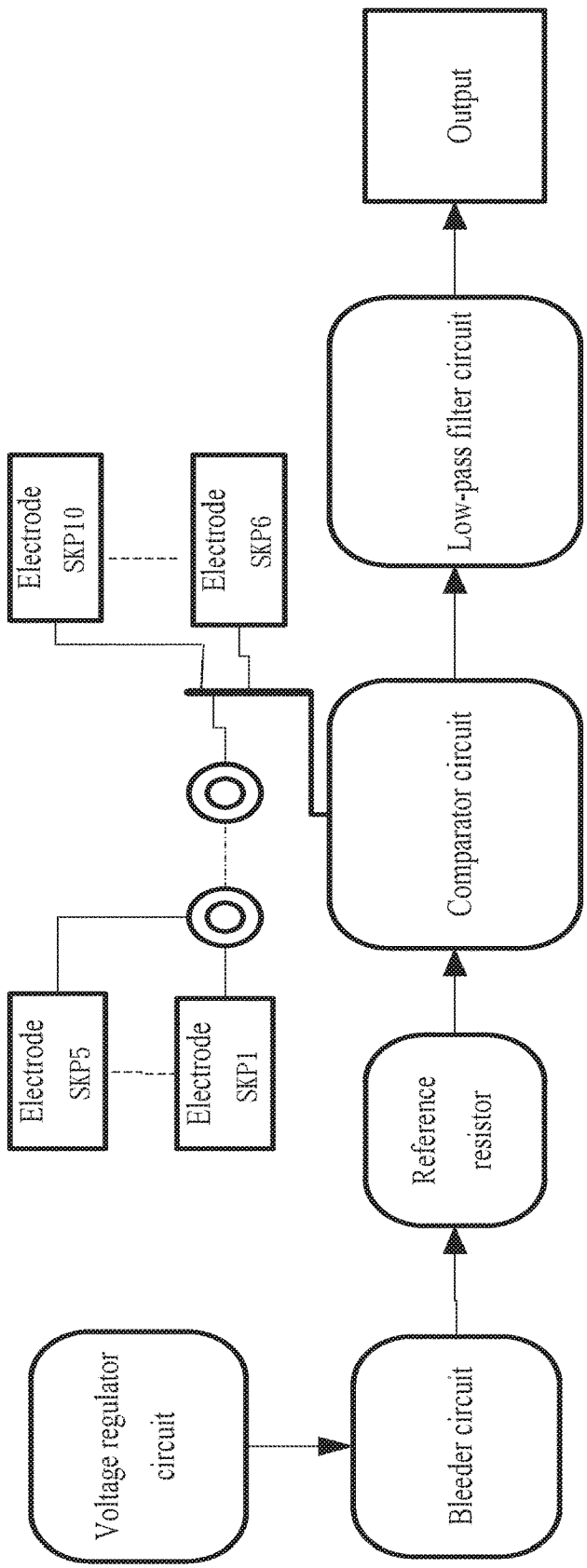
FIG. 10 is a block diagram of the skin impedance acquisition circuit according to an embodiment of the invention.

As shown in FIG. 1 and FIG. 2, a signal sensing glove for acquiring biological signals is provided, comprising two signal sensing gloves RL for acquiring biological signals comprising ECG which are respectively glove R and glove L. The glove R or the glove L is provided with a signal bus port U.

A metal body RP and a metal body YP for acquiring biological signals comprising ECG are respectively embedded on the inner walls of the glove R and the glove L, and a bus wiring port Rc and a bus wiring port Lc with at least one port wired are respectively embedded on the outer walls of the metal body RP and the metal body YP. The wiring port Rc is connected to the metal body RP and the wiring port Lc is connected to the metal body YP. A metal body BP for acquiring biological signals comprising ECG is embedded on an outer wall of at least one of the glove R and the glove L, or a metal body BP and a metal body GP for acquiring biological signals comprising ECG are respectively embedded on the outer walls of the glove R and the glove L. When the wiring port Rc is connected to the wiring port Lc, an electronic element or a signal circuit in the glove R in connection with the wiring port Rc can be communicated with an electronic element or a signal circuit in the glove L in connection with the wiring port Lc by means of a bridged interconnection between the wiring port Rc and the wiring port Lc.

The signal bus port U is connected to the wiring port Rc and the wiring port Lc, communicated with the signal circuit by means of a bridged interconnection between the wiring port Rc and the wiring port Lc, and also connected to the electrode metal body RP or the metal body YP or the metal body BP and the metal body GP embedded in the other glove.

The metal body RP and the metal body YP are stuck on the skin of upper limbs and communicated with the wiring port Rc and the wiring port Lc by wearing the signal sensing gloves RL distinct in the left and right hands, and then the signal sensing gloves RL are placed on the skin of lower limbs or abdomen adjacent to the lower limbs to make the metal body BP and the metal body GP stick on the skin of lower limbs or abdomen adjacent to the lower limbs, in order to achieve that some ports of the signal bus port U are connected to the metal body RP, the metal body YP and the metal body BP or connected to the metal body RP, the metal body YP, the metal body BP and the metal body GP, but the other ports are reserved for further circuit connection.

The signal sensing gloves RL are attached with a signal acquisition device S which is attached to one of the glove R and the glove L fixedly or detachably, and also connected to the signal bus port U.

The glove with the signal acquisition device S attached thereon is provided with a signal transmission device C, the signal transmission device C being provided with a first input port E, a first output port F, a second input port G and a second output port H.

The first input port E is connected to a signal output end of the signal acquisition device S. The first output port F and the second input port G of the signal transmission device C are served as a reservation circuit, and the second output port H of the signal transmission device C is connected to a signal input end of the signal acquisition device S. The reservation circuit is a device with CPU operational capability, comprising a hand-held mobile terminal T.

The signal sensing gloves combined with the signal acquisition device S, the signal transmission device C and the hand-held mobile terminal T attached on the gloves form a hand-held, medical, multi-channel biological information acquisition mobile terminal system.

When the signal acquisition device S is used for acquiring ECG limb lead signal, red, yellow, black and green electrodes of an ECG limb lead electrode of the signal acquisition device S in contact with the human body are the metal body RP, the metal body YP, the metal body BP and the metal body GP, respectively.

An outer wall of the glove with the signal acquisition device S attached thereon is provided with an electronic pickup stethoscope M fixedly or detachably. 1-10 good conductive metal electrodes SKP are embedded in a position where an inner wall of the glove R or the glove L is in contact with the fingertip pulp (Shi-xuan acupoint). Light dependent resistors R and light sources or light sources Lmp (Optical network link management protocol) of other wavelengths are embedded in a position where an inner wall of the glove R or the glove L is in contact with the distal finger pulp. The signal acquisition device S is connected to the electronic pickup stethoscope M, multiple electrodes SKP, multiple light dependent resistors R and light sources Lmp (Optical network link management protocol) of visible light wavelength or other wavelengths, respectively.

A method is used for controlling time division multiplexing circuit gating by a single-channel position control source. The method comprises providing a pulse counting unit and a multiplex separation unit. The pulse counting unit comprises an input signal input end CI and at least one control signal output end group COG. Each end of at least one control signal output end group COG is set with a binary digit to form a control signal comprising multiple binary digits by combination in terms of digit. The multiplex separation unit comprises at least one controlled signal input end group CIG. Each end of at least one controlled signal input end group CIG is set with a binary digit to form a controlled signal address by combination in terms of digit. The control signal output end group COG is connected to the controlled signal input end group CIG.

By inputting an amplitude-adjustable timing pulse signal to an input signal input end CI of the pulse counting unit, a varied binary digit is output by at least one control signal output end group COG of the pulse counting unit; the binary digit controls the controlled signal address value of the controlled signal input end group CIG of the multiplex separation unit to vary, regulates gating of at least one input signal input end group X and the output signal output end Y of the multiplex separation unit, and then restores a discrete signal proximity to the original shape of a multi-channel input signal from a signal output by one output signal output end Y by a time division multiplexing calculation method, to achieve controlling time division multiplexing channel function of the multiplex separation unit only by one timing pulse signal.

As shown in FIG. 3 to FIG. 10, the signal acquisition device S comprises an ECG acquisition circuit, a heart sound acquisition circuit, a blood volume pulse acquisition circuit, and a skin impedance acquisition circuit. The ECG acquisition circuit comprises a lead input interface, a buffer circuit, a shield actuation circuit, a right leg drive circuit, a pre-amplifier circuit, a two-stage amplifier circuit, a 106 Hz low-pass filter circuit, a 50 Hz trap circuit, and a post-amplifier circuit. The lead input interface is connected to the buffer circuit, and the shield actuation circuit and the right leg drive circuit. The buffer circuit is connected to the pre-amplifier circuit connected to the two-stage amplifier circuit, and the shield actuation circuit and the right leg drive circuit. The two-stage amplifier circuit is connected to the 106 Hz low-pass filter circuit connected to the 50 Hz trap circuit, and the 50 Hz trap circuit is connected to the post-amplifier circuit. The heart sound acquisition circuit comprises a main amplifier circuit, a low-pass filter circuit, a trap circuit, a post-amplifier circuit and an anti-interference device. The main amplifier circuit is connected to the low-pass filter circuit, and the low-pass filter circuit is connected to the trap circuit connected to the post-amplifier circuit. The anti-interference device is connected to two ends of the main amplifier circuit, and the value of the low-pass filter circuit is in the range of 1-6 Hz. The blood volume pulse acquisition circuit comprises a voltage regulator circuit, a red light irradiation circuit, a phototransistor circuit, a bridge circuit, an amplifier circuit and a filter circuit. The red light irradiation circuit is connected to the voltage regulator circuit connected to the phototransistor circuit, and a phototransistor circuit is connected to the bridge circuit connected to the amplifier circuit, and the amplifier circuit is connected to the filter circuit. Light dependent resistors R and light sources or light sources LMP of other wavelengths are embedded in a position where an inner wall of the glove R or the glove L is in contact with the distal finger pulp. When the fingers are inserted into the glove, the red light is irradiated on the light dependent resistors R by penetrating the fingers, so that the finger blood volume determines light transmittance of light source penetrating the fingers and also determines resistance variation of the light dependent resistors R so as to achieve the acquisition of the blood volume pulse. The skin impedance acquisition circuit comprises a voltage regulator circuit, a bleeder circuit, a reference resistor, a comparator circuit, a low-pass filter circuit and an output; the voltage regulator circuit is connected to a bleeder circuit connected to the reference resistor. The reference resistor is connected to the comparator circuit connected to the low pass filter circuit. 1-10 good conductive metal electrodes SKP are embedded in a position where an inner wall of the glove R or the glove L is in contact with the fingertip pulp. The glove R and the glove L are respectively provided with electrodes SKP1-SKP5 and electrodes SKP6-SKP10. So, the acquisition of the skin impedance is achieved by pressing the metal electrodes SKP on any two points on the skin, just like by pressing two probes of a universal meter.

The hand-held mobile terminal T comprises a CPU, a data processing unit, a liquid crystal display unit, wireless WIFI or a 3G module.

The hand-held mobile terminal has the functions of a tablet computer, and can achieve not less than 2 hours of continuous working time by selecting low-power full-function seven-inch touch screen and high-energy lithium-DC power supply manner. The terminal with this size can be held by single hand and put into a pocket of the medical staff, which is convenient and meets the requirements of clinical work of the medical staff.

Wireless technology as the wireless connection technology with low cost, short distance and standardized application establishes a special connection for communication environment between a fixed device and a mobile device on the basis of low-cost short-distance wireless connection. Moreover, the wireless technology and modular products thereof are mature and low cost. The invention achieves data transmission between the signal sensing gloves and the terminal by using wireless transmission technology, thus avoiding connection wire, having low cost and improving convenience on detection.

In this embodiment, when making a round of visits, the doctor or nurse may carry the hand-held mobile terminal, establish a connection to wireless routing of the supervisor by using WIFI function and remote desktop interconnection technology of the terminal, access the hospital local area network, log in the hospital information system (HIS) and the electronic medical record (EMR) system, fast access and consult hospitalized information, medical history, test and inspection results, and other vital signs information on the patients to make orders for test, inspection, treatment and other medical orders in real time according to the clinical rounds and changes in conditions of patients, and finally complete writing for a variety of medical documents and save documents. The results of patients after detection analysis can be simultaneously uploaded to the electronic medical records of the patients from the hand-held mobile terminal T, thus facilitating the medical staff to understand complete medical history of the patients in the next round or diagnosis, optimizing medical care process, avoiding human errors and improving work efficiency of the medical staff.

In summary, the invention provides a hand-held, medical, multi-channel biological information acquisition mobile terminal system, which has the characteristics of low power consumption, small size and low cost, and can achieve on-site acquisition function of a variety of biological information and the mobilization of electronic health records, wherein the system comprises two signal sensing gloves RL with a cable end embedded therein. One of the gloves is provided with a signal bus port U for pooled connection of acquisition signals. The signal sensing gloves RL further comprise a signal acquisition device S connected to the signal bus port U for use in acquiring a variety of biological signals comprising multi-channel interconnected ECG, heart sounds, finger blood volume pulse, and skin impedance etc., further, the signal sensing gloves RL also can save, carry out calculation analysis processing and intuitively display indexes of testee comprising ECG, phonocardiogram, pulse value, heart rate value, degree of blood oxygen saturation, and skin impedance value etc. by connecting with a mobile terminal T wirelessly or with a wired connection through a signal transmission device C.

A method for controlling time division multiplexing circuit gating by a single-channel position control source is provided, comprising a pulse counting unit and a multiplex separation unit. An output end of the pulse counting unit is served as a control signal of the multiplex separation unit and connected to a controlled signal input end of the multiplex separation unit, showing as multi-input-single-output or multi-output-single-input.

Compared with the prior art, the invention has the characteristics of stable connection, anti-misoperation and simple operation and fewer control channels needed for multi-channel connection, facilitates the realization of real-time detection and wireless mobile inspection functions of a variety of individual health information for medical staff, even for family and individual in the practice of medical service in community health, helps to optimize the medical procedure, strengthens the medical safety and quality and improves work efficiency.

The embodiments mentioned above which are described specifically and in details just describe one implementation way of the invention, and will form any limit to the scope of the invention. Without deviating from the design concept of the invention, for an ordinary person skilled in the art, the technical solutions of the invention may have various modifications and improvements, and these modifications and improvements shall fall into the protection scope of the invention. Therefore, the protection scope of the invention shall be subjected to the accompanying claims.

What is claimed is:

1. A signal sensing glove system comprising:
a first glove (R) and a second glove (L) for acquiring biological signals comprising ECG;
a first metal body (RP) for acquiring biological signals comprising ECG being embedded on inner walls of the first glove (R);
a second metal body (YP) for acquiring biological signals comprising ECG being embedded on inner walls of the second glove (L);
the first metal body (RP) being disposed inside the first glove (R);
the second metal body (YP) being disposed inside the second glove (L);
a first wiring port (Rc) and a second wiring port (Lc) with at least one port wired being respectively embedded on outer walls of the first metal body (RP) and the second metal body (YP);
the first wiring port (Rc) being disposed outside the first glove (R);
the second wiring port (Lc) being disposed outside the second glove (L);
the first wiring port (Rc) being connected to the first metal body (RP);
the second wiring port (Lc) being connected to the second metal body (YP);
a third metal body (BP) for acquiring biological signals comprising ECG being embedded on the outer walls of the first glove (R);
a fourth metal body (GP) for acquiring biological signals comprising ECG being embedded on the outer walls of the second glove (L);
the third metal body (BP) being disposed outside the first glove (R);
the fourth metal body (GP) being disposed outside the second glove (L);
in response to the first wiring port (Rc) being connected to the second wiring port (Lc), a signal circuit in the first glove (R) in connection with the first wiring port (Rc) being communicated with a signal circuit in the second glove (L) in connection with the second wiring port (Lc) by an interconnection between the first wiring port (Rc) and the second wiring port (Lc);
the first wiring port (Rc) being in the interconnection with the second wiring port (Lc);
a signal bus port (U) being connected to the first wiring port (Rc) and the second wiring port (Lc), communicated with the signal circuit in the first glove (R) and the signal circuit in the second glove (L), and connected to the first metal body (RP) or the second metal body (YP) or the third metal body (BP) and the fourth metal body (GP);
the first metal body (RP) and the second metal body (YP) being stuck on skin of upper limbs and communicated with the first wiring port (Rc) and the second wiring port (Lc) by wearing the first and second gloves (R, L) distinct in left and right hands;

the first glove (R) and the second glove (L) being placed on skin of lower limbs or an abdomen adjacent to the lower limbs to make the third metal body (BP) and the fourth metal body (GP) stick on the skin of lower limbs or the abdomen adjacent to the lower limbs;

a portion of the signal bus port (U) being connected to the first metal body (RP), the second metal body (YP), the third metal body (BP) and the fourth metal body (GP);

a remaining portion of the signal bus port (U) being reserved for circuit connection;

a signal acquisition device (S);

the signal acquisition device (S) being attached to one of the first glove (R) and the second glove (L) and connected to the signal bus port (U);

the signal acquisition device (S) comprising a blood volume pulse acquisition circuit;

the blood volume pulse acquisition circuit comprising a voltage regulator circuit, a red light irradiation circuit, a phototransistor circuit, a bridge circuit, an amplifier circuit and a filter circuit;

the red light irradiation circuit being connected to the voltage regulator circuit;

the voltage regulator circuit being connected to the phototransistor circuit;

the phototransistor circuit being connected to the bridge circuit;

the bridge circuit being connected to the amplifier circuit; and the amplifier circuit being connected to the filter circuit.

2. The signal sensing glove system of claim 1 comprising:
the glove with the signal acquisition device (S) attached thereon being provided with a signal transmission device (C), the signal transmission device (C) being provided with a first input port (E), a first output port (F), a second input port (G) and a second output port (H); and the first input port (E) of the signal transmission device (C) being connected to a signal output end of the signal acquisition device (S), the second output port (H) of the signal transmission device (C) being connected to a signal input end of the signal acquisition device (S), the first output port (F) and the second input port (G) each being reserved for a device with CPU operational capability, the device with CPU operational capability comprising a hand-held mobile terminal (T).

3. The signal sensing glove system of claim 2 comprising:
the hand-held mobile terminal (T) comprising a CPU, a data processing unit, a liquid crystal display unit, wireless WIFI or a 3G module.

4. The signal sensing glove system of claim 2 comprising:
in response to the signal acquisition device (S) being used for acquiring an ECG limb lead signal, red, yellow, black and green electrodes of an ECG limb lead electrode, in contact with the human body, of the signal acquisition device (S) being the first metal body (RP) as the red electrode, the second metal body (YP) as the yellow electrode, the third metal body (BP) as the black electrode and the fourth metal body (GP) as the green electrode, respectively.

5. The signal sensing glove system of claim 2 comprising:
an electronic pickup stethoscope (M);
the electronic pickup stethoscope (M) being fixedly or detachably provided on an outer wall of the glove with the signal acquisition device (S) attached thereon;
1-10 conductive metal electrodes (SKP) being embedded in a position where an inner wall of the first glove (R) or the second glove (L) is in contact with a fingertip pulp, light dependent resistors (R) and light sources (Lmp) of visible light wavelength or other wavelengths being embedded in a position where the inner wall of the first glove (R) or the second glove (L) is in contact with the fingertip pulp; and the signal acquisition device (S) being connected to the electronic pickup stethoscope (M), multiple electrodes (SKP), multiple light dependent resistors (R) and light sources (Lmp) of visible light wavelength or other wavelengths, respectively.

6. The signal sensing glove system of claim 1 comprising:
in response to the signal acquisition device (S) being used for acquiring an ECG limb lead signal, red, yellow, black and green electrodes of an ECG limb lead electrode of the signal acquisition device (S) in contact with the human body being the first metal body (RP) as the red electrode, the second metal body (YP) as the yellow electrode, the third metal body (BP) as the black electrode and the fourth metal body (GP) as the green electrode, respectively.

7. The signal sensing glove system of claim 1 comprising:
an electronic pickup stethoscope (M);
the electronic pickup stethoscope (M) being fixedly or detachably provided on an outer wall of the glove with the signal acquisition device (S) attached thereon;
1-10 conductive metal electrodes (SKP) being embedded in a position where an inner wall of the first glove (R) or the second glove (L) is in contact with a fingertip pulp, light dependent resistors (R) and light sources (Lmp) of visible light wavelength or other wavelengths being embedded in a position where the inner wall of the first glove (R) or the second glove (L) is in contact with the fingertip pulp; and the signal acquisition device (S) being connected to the electronic pickup stethoscope (M), multiple electrodes (SKP), multiple light dependent resistors (R) and light sources (Lmp) of visible light wavelength or other wavelengths, respectively.

8. The signal sensing glove system of claim 1 comprising:
the signal acquisition device (S) comprising an ECG acquisition circuit, a heart sound acquisition circuit and a skin impedance acquisition circuit.

9. The signal sensing glove system of claim 8 comprising:
the ECG acquisition circuit comprising a lead input interface, a buffer circuit, a shielding drive circuit, a right leg drive circuit, a pre-amplifier circuit, a two-stage amplifier circuit, a 106 Hz low-pass filter circuit, a 50 Hz circuit, and a post-amplifier circuit; and the lead input interface being connected to the buffer circuit, the shielding drive circuit and the right leg drive circuit, the buffer circuit being connected to the pre-amplifier circuit, the pre-amplifier circuit being connected to the two-stage amplifier circuit, the shielding drive circuit and the right leg drive circuit, the two-stage amplifier circuit being connected to the 106 Hz low-pass filter circuit, the 106 Hz low-pass filter circuit being connected to the 50 Hz circuit, the 50 Hz circuit being connected to the post-amplifier circuit.

10. The signal sensing glove system of claim 8 comprising:
the heart sound acquisition circuit comprising a main amplifier circuit, a low-pass filter circuit, a 50 Hz circuit, a post-amplifier circuit and an anti-interference device;

the main amplifier circuit being connected to the low-pass filter circuit, the low-pass filter circuit being connected to the 50 Hz circuit, the 50 Hz circuit being connected to the post-amplifier circuit, the anti-interference device being connected to two ends of the main amplifier circuit; and the value of the low-pass filter circuit being 106 Hz.

11. The signal sensing glove system of claim 8 comprising:

the skin impedance acquisition circuit comprising a voltage regulator circuit, a reference resistor, a comparator circuit, a low-pass filter circuit and an output; and the voltage regulator circuit being connected to the reference resistor, the reference resistor being connected to the comparator circuit, the comparator circuit being connected to the low pass filter circuit.

\* \* \* \* \*